US00PP22041P2

(12) United States Plant Patent
Crowther

(10) Patent No.: US PP22,041 P2
(45) Date of Patent: Jul. 26, 2011

(54) ***GEUM* PLANT NAMED 'TOTALLY TANGERINE'**

(50) Latin Name: *Geum chiloense×rivale*
Varietal Denomination: Totally Tangerine

(76) Inventor: Timothy Crowther, Arundel (GB)

( * ) Notice: Subject to any disclaimer, the term of this patent is extended or adjusted under 35 U.S.C. 154(b) by 0 days.

(21) Appl. No.: 12/660,853

(22) Filed: Mar. 5, 2010

Related U.S. Application Data

(60) Provisional application No. 61/210,546, filed on Mar. 20, 2009.

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Susan McCormick Ewoldt

(57) ABSTRACT

A new cultivar of *Geum* plant named 'TOTALLY TANGERINE' that is characterized by clumping habit, dark green leaves, and delicate sterile orange-peach flowers borne in profusion and blooming from early spring to late fall. In combination these traits set 'TOTALLY TANGERINE' apart from all other existing varieties of *Geum* known to the inventor.

3 Drawing Sheets

Genus: *GEUM.*
Species: *chiloense×rivale.*
Denomination: 'TOTALLY TANGERINE'.

BACKGROUND OF THE INVENTION

This application claims the benefit of priority under 35 U.S.C. 119(e) of U.S. Provisional Application No. 61/210,546 filed on Mar. 20, 2009, entitled *Geum* Plant named 'TOTALLY TANGERINE'.

The present invention relates to a new and distinct cultivar of *Geum* plant, commonly named Avens, which is grown as an ornamental sub-shrub for garden and landscape. The new cultivar is known botanically as *Geum chiloense×rivale* from the family Rosaceae, and will be referred to hereinafter by the cultivar name 'TOTALLY TANGERINE'.

'TOTALLY TANGERINE' is a hybrid seedling selection derived from the deliberate cross-pollination between a plant of *Geum rivale* (species, unpatented) as female parent and a plant of *Geum chiloense* 'Mrs. Bradshaw' (unpatented) as the male parent. The inventor conducted cross-pollination at the inventor's nursery in West Sussex, United Kingdom.

Breeding began in 1998 when the inventor grew out the parents to flowering. Emasculating the flowers of *Geum rivale,* the inventor secured pollen from the flowers of *Geum chiloense* 'Mrs. Bradshaw' and with this pollen the inventor fertilized the flowers of *Geum rivale.* Resulting seed was collected from both parents and sown by the inventor in spring 1999. The inventor selected 'TOTALLY TANGERINE' from the resulting flowering progeny in summer 1999. Selection was based on the criteria of early flowering, long prolific bloom season, flower color, and flower aspect.

In regards to flower quantity, flower color, and bloom period there are no comparison plants known to the inventor. 'TOTALLY TANGERINE' is distinguishable from both parents by long bloom season, prolific flowering, and sterility. While both parents bear bristly fruit, 'TOTALLY TANGERINE' has not been found to produce fruit or seed during repeated observations.

'TOTALLY TANGERINE' is distinguishable from the female parent by flower color and flower aspect. The female parent *Geum rivale* exhibits downward facing cream-yellow flowers.

'TOTALLY TANGERINE' is distinguishable from the male parent by flower color, flower quantity, and flower form. The male parent *Geum chiloense* 'Mrs. Bradshaw' exhibits scarlet semi-double ruffled flowers.

'TOTALLY TANGERINE' exhibits long floriferous bloom season, clumping habit, dark green foliage, and delicate orange-peach flowers that gradually fade with exposure to full sunlight. Flowers are single, facing upward and outward. Flowering season is from early spring to late fall. 'TOTALLY TANGERINE' reaches 90 cm. in height and 60 cm. in width at one year of age, and achieves a height of 130 cm. and a spread of 100 cm. at maturity. Hardiness is classified as USDA Zone 4. 'TOTALLY TANGERINE' is observed to be sterile, producing no fruit or seed.

The first asexual reproduction of 'TOTALLY TANGERINE' was accomplished in 2003. The inventor conducted the asexual propagation at the inventor's nursery in West Sussex, United Kingdom. The method used was division. Since that time, under careful observation, the unique characteristics of 'TOTALLY TANGERINE' have been fixed, stable, uniform, and reproduce true to type in successive generations of asexual reproduction.

SUMMARY OF THE INVENTION

The following represent the distinguishing characteristics of 'TOTALLY TANGERINE'. These traits in combination distinguish 'TOTALLY TANGERINE' as a new and distinct cultivar apart from all other existing varieties of *Geum* known to the inventor. 'TOTALLY TANGERINE' has not been tested under all possible conditions and phenotypic differences may be observed with variations in environmental, climatic, and cultural conditions, however, without any variance in genotype.

1. 'TOTALLY TANGERINE' is extremely floriferous.
2. 'TOTALLY TANGERINE' flowers over a long period, typically from early spring to late fall.

3. The flowers of 'TOTALLY TANGERINE' face upward and outward.
4. The flowers of 'TOTALLY TANGERINE' are single with overlapping petals.
5. The flowers of 'TOTALLY TANGERINE' are orange-peach in color, becoming paler when exposed to full sunlight.
6. After one year of growth, a plant of 'TOTALLY TANGERINE' achieves a height of approximately 90 cm. and a spread of 60 cm.
7. At maturity a plant of 'TOTALLY TANGERINE' achieves a height of approximately 130 cm. and a spread of 100 cm.
8. 'TOTALLY TANGERINE' is hardy in USDA Zone 4.
9. 'TOTALLY TANGERINE' has been observed to produce no fruit or seed.

BRIEF DESCRIPTION OF THE DRAWINGS

The accompanying color drawings illustrate the overall appearance of 'TOTALLY TANGERINE' showing the color of its foliage and flowers as true as it is reasonably possible to obtain in color reproductions of this type. Color in the drawings may differ from color values cited in the detailed botanical description, which accurately describe the actual color of the new variety 'TOTALLY TANGERINE'.

The drawing labeled

The drawing labeled

The drawing labeled

Figure 1:
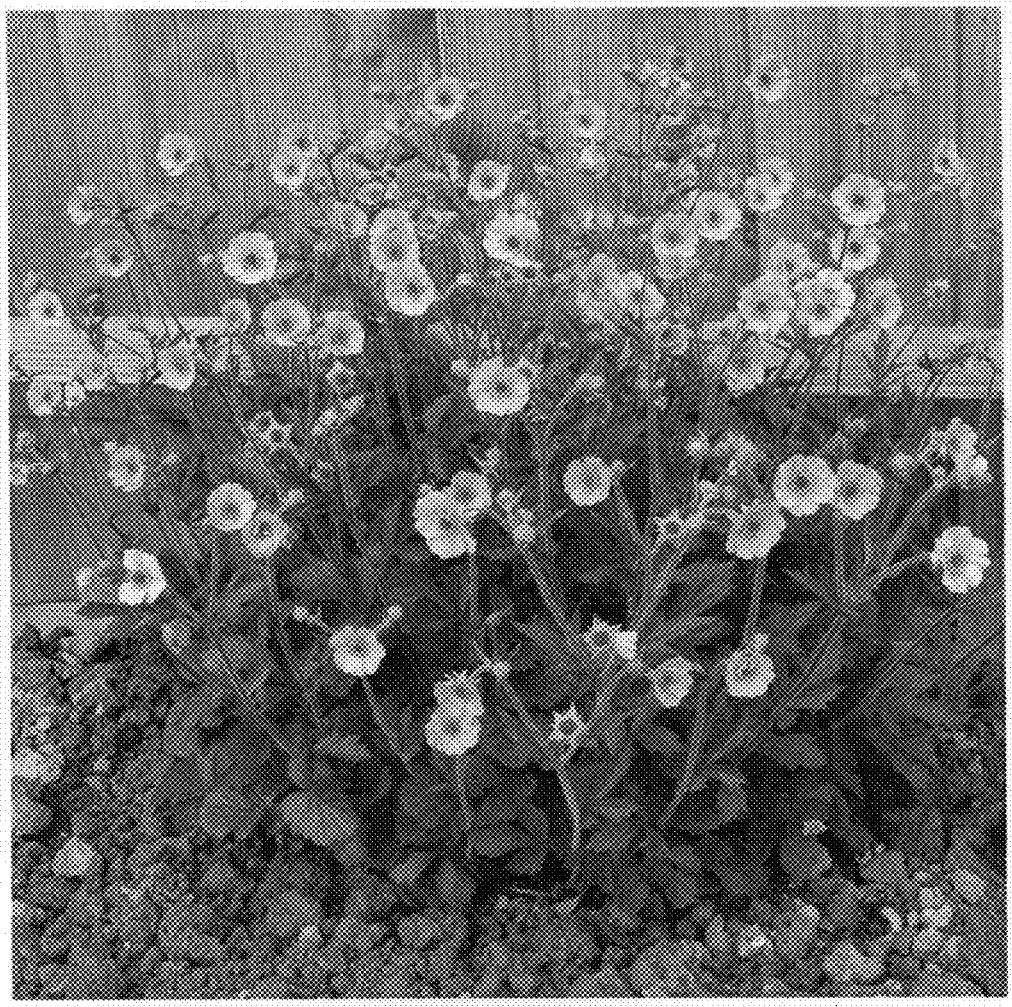
FIG. 1 depicts a two-year-old plant of 'TOTALLY TANGERINE' growing out-of-doors in West Sussex, United Kingdom.
Figure 2:
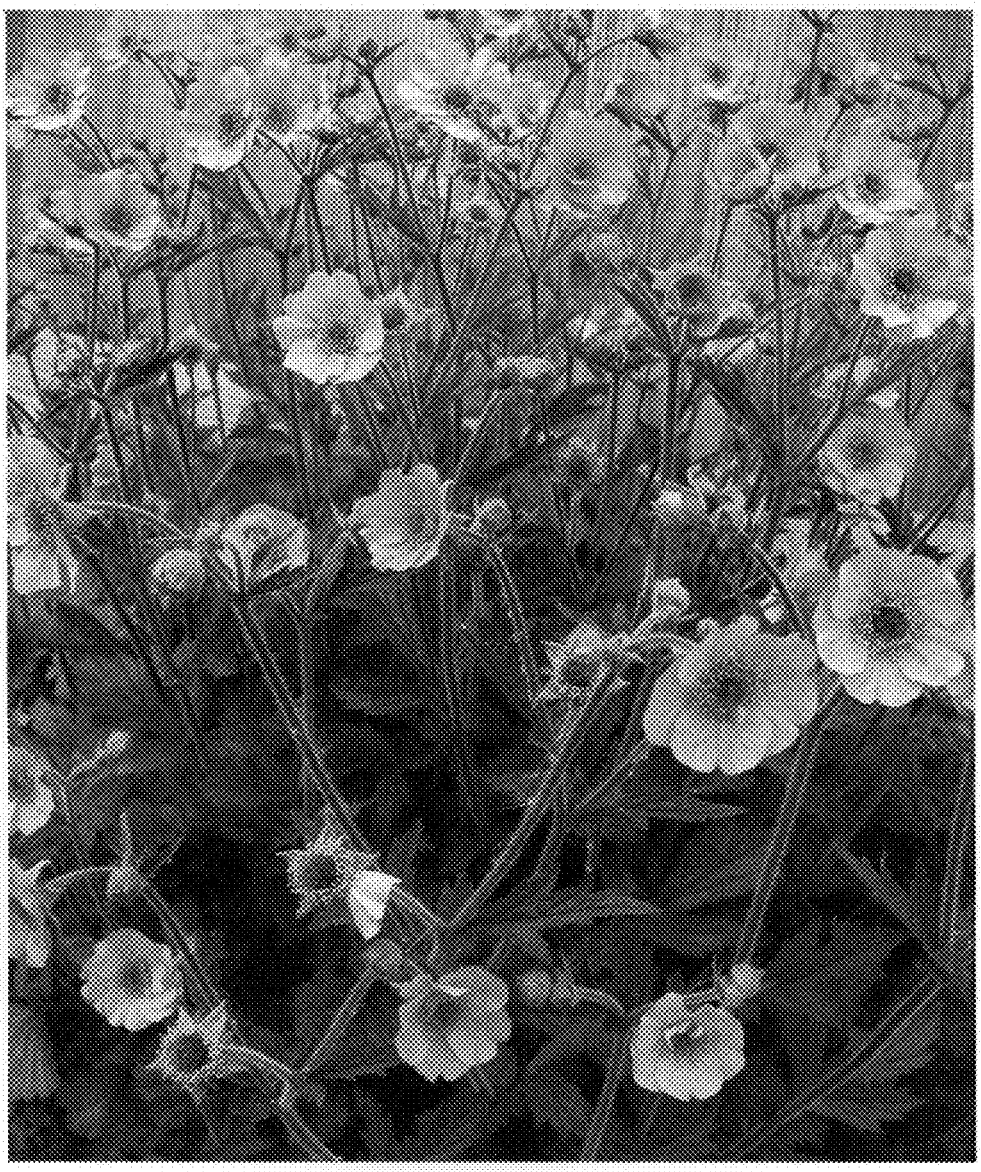
FIG. 2 depicts a close-up view of the flower stems, flower buds, and flowers of the plant 'TOTALLY TANGERINE' which is illustrated in FIG. 1.
Figure 3:
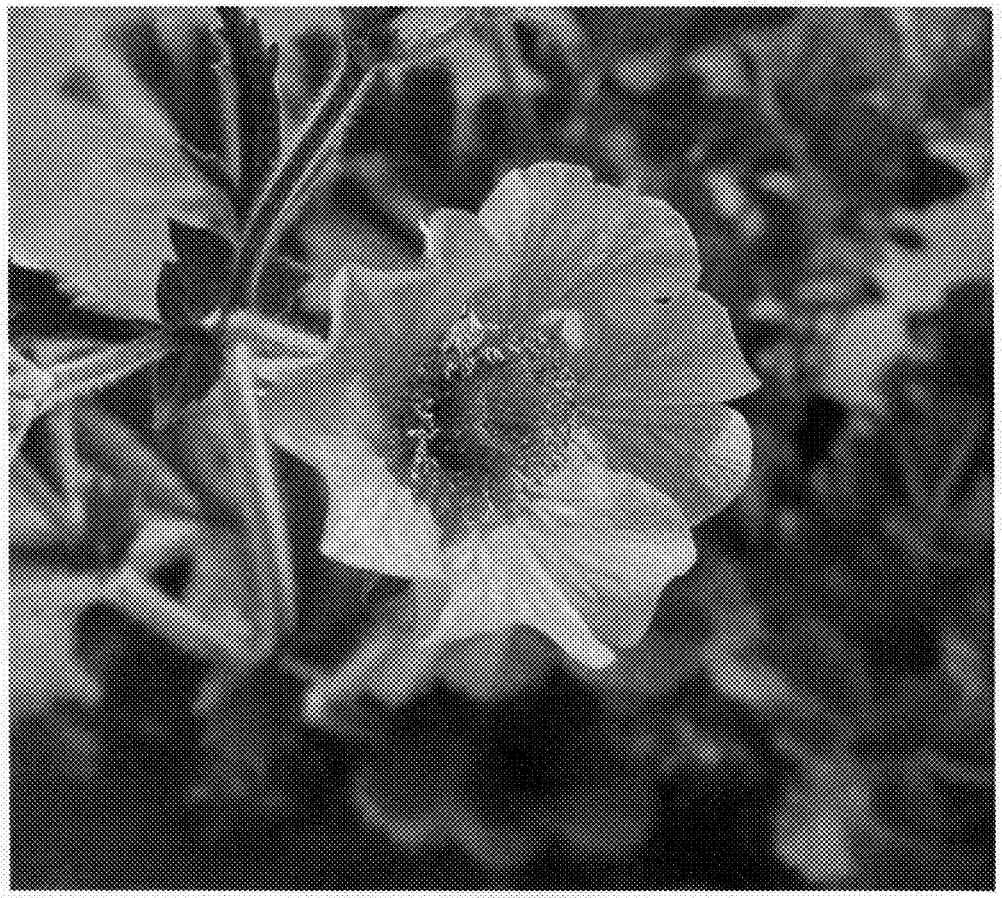
FIG. 3 depicts a close-up view of a flower of 'TOTALLY TANGERINE'.

All three drawings have been made using conventional techniques and although colors may appear different from actual colors due to light reflectance, they are as accurate as possible by conventional photography.

DETAILED BOTANICAL DESCRIPTION OF THE PLANT

The following is a detailed description of 'TOTALLY TANGERINE'. Data was collected from 12 month old 2-gallon container plants grown out-of-doors in Arroyo Grande, Calif. The color determinations are in accordance with the 2001 edition of The Colour Chart of the Royal Horticultural Society, London, England, except where general color terms of ordinary dictionary significance are used. Growing requirements are similar to the species.

Botanical classification: *GEUM chiloense×rivale* 'TOTALLY TANGERINE'.
Family: Rosaceae.
Species: *chiloense×rivale.*
Denomination: 'TOTALLY TANGERINE'.
Common name: Avens.
Commercial category: Ornamental sub-shrub.
Recommended container size: 1-liter.
Type: Perennial.
Use: For garden and landscape.
Parentage: *GEUM chiloense×rivale* 'TOTALLY TANGERINE' is a hybrid seedling selection derived from the deliberate cross-pollination of the following parents:
- *Female parent.*—*Geum rivale* (species, unpatented).
- *Male parent.*—*Geum chiloense* 'Mrs. Bradshaw' (unpatented).

Vigor: Vigorous
Growth habit: Clumping.
Plant shape: Mound.
Dimensions (in first year): 90 cm. in height and 60 cm. in width.
Mature dimensions: 130 cm. in height and 100 cm. in width.
Hardiness: USDA Zone 4.
Propagation: Division.
Time to initiate roots: Approximately 30 days are required to produce roots on an initial cutting.
Crop time: Approximately 9 months are needed to achieve a finished 1-liter plant in flower from an un-rooted cutting.
Root system: Fibrous.
Cultural requirements: Well-draining rocky soil, plentiful water, and filtered to full sunlight.
Seasonal interest: Floriferous display of delicate orange peach flowers.
Disease and pest resistance: None known to the inventor.
Disease and pest susceptibility: Those typical to *Geum* species and cultivars.

Stem:
- *Branching habit.*—Sparsely branched.
- *Stem shape.*—Sub-cylindrical.
- *Stem length* (*average*).—10 cm.
- *Stem width* (*average*).—0.40 cm.
- *Stem color.*—144A.
- *Stem surface.*—Villous.
- *Internode length.*—1.50 cm.

Foliage:
- *Type.*—Evergreen.
- *Arrangement.*—Cauline.
- *Attachment.*—Sessile.
- *Leaf shape.*—Deltoid.
- *Vein pattern.*—Pinnate.
- *Vein color* (*abaxial surface*).—137D.
- *Vein color* (*adaxial surface*).—137A.
- *Leaf margin.*—Biserrate.
- *Leaf division.*—Simple.
- *Leaf appearance.*—Semi-glossy.
- *Leaf color* (*abaxial surface*).—137C.
- *Leaf color* (*adaxial surface*).—137A.
- *Leaf surface* (*abaxial surface*).—Floccose.
- *Leaf surface* (*adaxial surface*).—Villous.
- *Stipule color.*—137A.
- *Stipule shape.*—Triangular.
- *Stipule surface.*—Villous.
- *Stipule dimensions.*—2 mm. in length and 1.50 mm. in width.
- *Leaf Length* (*range*).—3.75-6 cm.
- *Leaf width* (*range*).—1.50-7.50 cm.
- *Leaf apex.*—Sub-acute.
- *Leaf base.*—Truncate.

Inflorescence:
- *Type.*—Solitary flower bearing small secondary bracteoles at the base of the calyx.
- *Aspect* (*range*).—Facing upward and outward.
- *Bloom season* (*range*).—Early spring through fall.
- *Inflorescence dimensions.*—1.50 cm. in depth and 4 cm. in diameter.
- *Inflorescence fragrance.*—None observed.
- *Inflorescence quantity* (1-*liter container plant*).—Average of 25.
- *Inflorescence quantity* (*mature plant*).—Average of 65.
- *Lastingness of inflorescence* (*range*).—2-5 days on plant.

*Bud shape.*—Rounded pyramidal to ovoid.
*Bud dimensions.*—1 cm. in height and 1 cm. in diameter.
*Bud apex.*—Acute.
*Bud base.*—Rounded.
*Bud surface.*—Floccose.
*Bud color.*—144A.
*Petal* (*range*).—6-10 in number.
*Petal color* (*abaxial surface*).—31A, fades to 168B.
*Petal color* (*adaxial surface*).—32A, fades to 169C.
*Petal vein color* (*abaxial and adaxial surface*).—31A.
*Petal margin.*—Entire.
*Petal apex.*—Retuse.
*Petal base.*—Truncate.
*Petal shape* (*range*).—Orbicular to reniform.
*Petal dimensions* (*average*).—1.60 cm. in height and 2.00 cm. in width.
*Petals fused or unfused.*—Unfused.
*Petal texture.*—Lightly crisped.
*Self-cleaning or persistent.*—Self-cleaning.
*Peduncle dimensions* (*range*).—2.50-7 cm. in length.
*Peduncle width* (*range*).—0.25-0.50 cm. in width.
*Peduncle color.*—N199B.
*Peduncle surface.*—Floccose.
*Peduncle shape.*—Sub-cylindrical.
*Calyx shape.*—Stellate.
*Calyx diameter.*—3 cm.
*Sepals.*—5 in number.
*Sepals fused or unfused.*—Unfused.
*Sepal shape.*—Lanceolate.
*Sepal margins.*—Entire.
*Sepal dimensions.*—1 cm. in length and 0.50 cm. in width.
*Sepal color* (*abaxial surface*).—138B.
*Sepal color* (*adaxial surface*).—138C.
*Sepal surface* (*adaxial and abaxial*).—Floccose.
*Sepal apex.*—Acute.
*Sepal base.*—Truncate.
*Bracteole.*—5 in number.
*Bracteole fused or unfused.*—Unfused.
*Bracteole shape.*—Lanceolate.
*Bracteole margin.*—Entire.
*Bracteole dimensions.*—3 mm. in length and 1.5 mm. in width.
*Bracteole color* (*abaxial and adaxial surface*).—138B.
*Bracteole surface* (*abaxial and adaxial*).—Floccose.
*Bracteole apex.*—Acute.
*Bracteole base.*—Rounded.

Reproductive organs:
*Stamen.*—Very many: 75 or more in number.
*Stamen length.*—6 mm.
*Filament color.*—151B.
*Anther color.*—17A.
*Pollen color.*—17A.
*Style.*—Very many: 75 or more in number.
*Style length.*—6 mm.
*Style shape.*—Filiform and geniculate at tip.
*Style color.*—172A.
*Ovary position.*—Inferior.
*Ovary color.*—147A.
*Ovary shape.*—Pyramidal.
*Ovary dimensions.*—3 mm. in height and 2 mm. in width.

Seed: None present. Variety is sterile.

It is claimed:

1. A new and distinct variety of *Geum* plant named 'TOTALLY TANGERINE' as described and illustrated herein.

* * * * *